United States Patent
Dr et al.

(10) Patent No.: US 9,278,932 B1
(45) Date of Patent: Mar. 8, 2016

(54) PROCESS FOR PREPARATION OF 2-CHLORO-N-(4-CHLORO-3-PYRIDIN-2-YLPHENYL)-4-METHYLSULFONYL-BENZAMIDE SOLID FORMS

(71) Applicants: Rafiuddin Dr, Raichur (IN); Vinod Kumar Singh, Raichur (IN); Nagnnath Kokare, Raichur (IN); Akshaykant Chaturvedi, Raichur (IN)

(72) Inventors: Rafiuddin Dr, Raichur (IN); Vinod Kumar Singh, Raichur (IN); Nagnnath Kokare, Raichur (IN); Akshaykant Chaturvedi, Raichur (IN)

(73) Assignee: SHILPA MEDICARE LIMITED, Raichur, Karnataka (IN)

(*) Notice: Subject to any disclaimer, the term of this patent is extended or adjusted under 35 U.S.C. 154(b) by 0 days.

(21) Appl. No.: 14/773,322

(22) PCT Filed: Mar. 5, 2014

(86) PCT No.: PCT/IB2014/059442
§ 371 (c)(1),
(2) Date: Sep. 5, 2015

(87) PCT Pub. No.: WO2014/147504
PCT Pub. Date: Sep. 25, 2014

(30) Foreign Application Priority Data

Mar. 22, 2013 (IN) .............. 1248/CHE/2013
Mar. 26, 2013 (IN) .............. 1315/CHE/2013

(51) Int. Cl.
*C07D 213/38* (2006.01)
*C07D 213/40* (2006.01)
*C07F 5/04* (2006.01)

(52) U.S. Cl.
CPC ............ *C07D 213/40* (2013.01); *C07D 213/38* (2013.01); *C07F 5/04* (2013.01)

(58) Field of Classification Search
None
See application file for complete search history.

(56) References Cited

U.S. PATENT DOCUMENTS

| 7,888,364 B2 | 2/2011 | Gunzner et al. |
| 2009/0281089 A1 | 11/2009 | Gunzner et al. |

FOREIGN PATENT DOCUMENTS

| CN | 102731373 A | 10/2012 |
| CN | 102731373 T | 10/2012 |

*Primary Examiner* — Zinna Northington Davis (57) ABSTRACT

The present invention relates to crystalline 2-Chloro-N-(4-chloro-3-pyridin-2-ylphenyl)-4-methylsulfonylbenzamide (I) designated as Form-SV and process for preparation thereof.

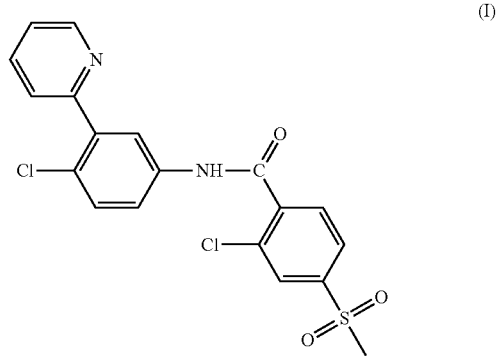

The invention further relates to pharmaceutical compositions comprising crystalline Form-SV or non-crystalline form of (2-chloro-N-(4-chloro-3-(pyridin-2-yl)phenyl)-4-(methyl-sulfonyl)benzamide, useful in the treatment of cancer.

8 Claims, 3 Drawing Sheets

PROCESS FOR PREPARATION OF 2-CHLORO-*N*-(4-CHLORO-3-PYRIDIN-2-YLPHENYL)-4-METHYLSULFONYL-BENZAMIDE SOLID FORMS

FIELD OF THE INVENTION

The present invention relates to crystalline 2-Chloro-N-(4-chloro-3-pyridin-2-ylphenyl)-4-methylsulfonylbenzamide (I) designated as Form-SV and process for preparation thereof.

(I)

The invention further relates to pharmaceutical compositions comprising crystalline Form-SV or non-crystalline form of (2-chloro-N-(4-chloro-3-(pyridin-2-yl)phenyl)-4-(methylsulfonyl)benzamide, useful in the treatment of cancer.

INTRODUCTION

Particular aspects of the present application relate to process for preparation of a crystalline form of (2-chloro-N-(4-chloro-3-(pyridin-2-yl)phenyl)-4-(methylsulfonyl)benzamide or Vismodegib, designated as Form-SV. The invention of the present application further relates to pharmaceutical compositions comprising crystalline Form-SV or non-crystalline form of 2-chloro-N-(4-chloro-3-(pyridin-2-yl)phenyl)-4-(methylsulfonyl)benzamide useful in the treatment of cancer.

Vismodegib was approved by USFDA on January 2012 and is marketed under the trade name ERIVEDGE™. It is chemically mentioned in the USFDA label as (2-chloro-N-(4-chloro-3-(pyridin-2-yl)phenyl)-4-(methylsulfonyl)benzamide (I). Vismodegib is a crystalline free base and is a white to tan coloured crystalline powder having pH dependent solubility.

(I)

Gunzner et al in U.S. Pat. No. 7,888,364 provide the first disclosure of (2-chloro-N-(4-chloro-3-(pyridin-2-yl)phenyl)-4-(methylsulfonyl)benzamide (also known as Vismodegib), which also describes the process for preparing (2-chloro-N-(4-chloro-3-(pyridin-2-yl)phenyl)-4-(methylsulfonyl)benzamide.

Gunzner et al further in US2009281089 disclose a process for preparation of (2-chloro-N-(4-chloro-3-(pyridin-2-yl)phenyl)-4-(methylsulfonyl)benzamide by reacting organometallic-pyridyl compound with a chloro-substituted nitrobenzene, followed by reduction and coupling reaction with mesyl and chloro substituted benzoic acid derivatives.

As of now, only polymorphism detail that is known for (2-chloro-N-(4-chloro-3-(pyridin-2-yl)phenyl)-4-(methylsulfonyl)benzamide, is in USFDA label, where it has been described as a crystalline powder, but no characterization details are available for the said crystalline form. Polymorphism has increasingly become relevant to the drugs with oral dosage forms due to its apparent relation to dose preparation/suitability in composition steps/bioavailability and other pharmaceutical profiles. Polymorphism is known to be peculiar phenomenon in solid materials, wherein existence of different physical forms including shape, size, and arrangement of molecules in the physical state or polymorphs of same compound are known to exist in the natural and other conditions.

A single compound, or a salt complex, may give rise to a variety of solids having distinct physical properties, which often results in substantial differences in bioavailability, stability, and other differences between production lots of formulated pharmaceutical products. Since polymorphic forms can vary in their chemical and physical properties, regulatory authorities often require that efforts be made to identify all possible polymorphic forms, e.g., hydrate or anhydrate, crystalline or amorphous, solvated or un-solvated forms, etc. of the drug substances. However, the existence, and possible numbers, of polymorphic forms for a given compound may not be predicted. In addition, there are no "standard" procedures that can be applied/utilized to prepare different polymorphic forms of a substance. Moreover, it is often uncertain for a chemical entity-whether any polymorphism phenomenon exists in the molecule or not.

Nevertheless, new forms of pharmaceutically active/useful compounds may provide an opportunity to improve the drug performance characteristics of such product. Hence, it was thought worthwhile to explore new stable and usable forms of (2-chloro-N-(4-chloro-3-(pyridin-2-yl)phenyl)-4-(methylsulfonyl)benzamide and processes for their preparation, which may be cost-effective and industrially amenable. Thus scientists of the present invention provide stable crystalline and non-crystalline form of (2-chloro-N-(4-chloro-3-(pyridin-2-yl)phenyl)-4-(methylsulfonyl)benzamide, along with economical and industrially viable processes for preparation thereof.

SUMMARY OF INVENTION

Particular aspects of the present application relate to the process for the preparation crystalline (2-chloro-N-(4-chloro-3-(pyridin-2-yl)phenyl)-4-(methylsulfonyl)benzamide (I), designated as Form-SV.

(I)

The application further relates to processes for preparation of non-crystalline form of (2-chloro-N-(4-chloro-3-(pyridin-2-yl)phenyl)-4-(methylsulfonyl)benzamide, substantially free from process related impurities. The crystalline polymorphic Form-SV or non-crystalline form of (2-chloro-N-(4-chloro-3-(pyridin-2-yl)phenyl)-4-(methylsulfonyl)benzamide obtained by the processes according to the present invention may be useful as active pharmaceutical ingredient in pharmaceutical compositions for the treatment of cancer. Different aspects of the present application are summarized herein below individually.

In one aspect of the present application, the present invention provides a crystalline form of (2-chloro-N-(4-chloro-3-(pyridin-2-yl)phenyl)-4-(methylsulfonyl)benzamide, designated as Form-SV characterized by X-ray powder diffraction pattern having at least five diffraction angle 2θ° peaks selected from peak set of 9.5, 10.7, 12.2, 15.8, 16.7, 17.4, 21.4, 24.0 and 26.0±0.2θ° and DSC isotherm comprising at least one endothermic peak ranging between 165 to 185° C.

Figure 1:
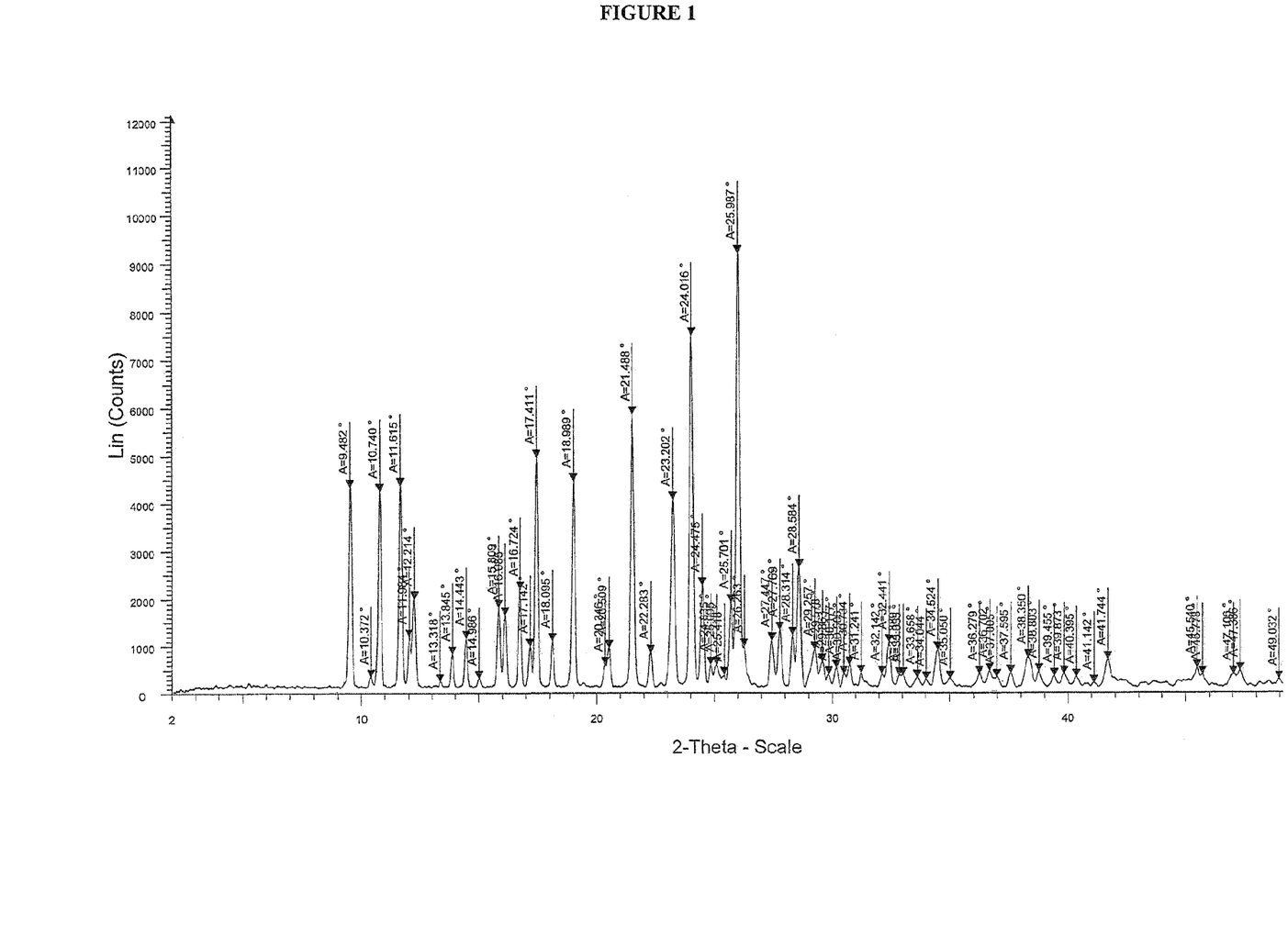
FIG. 1 is an example of X-ray powder diffraction ("XRPD") pattern of crystalline 2-Chloro-N-(4-chloro-3-pyridin-2-ylphenyl)-4-methylsulfonylbenzamide designated as Form-SV.
Figure 2:
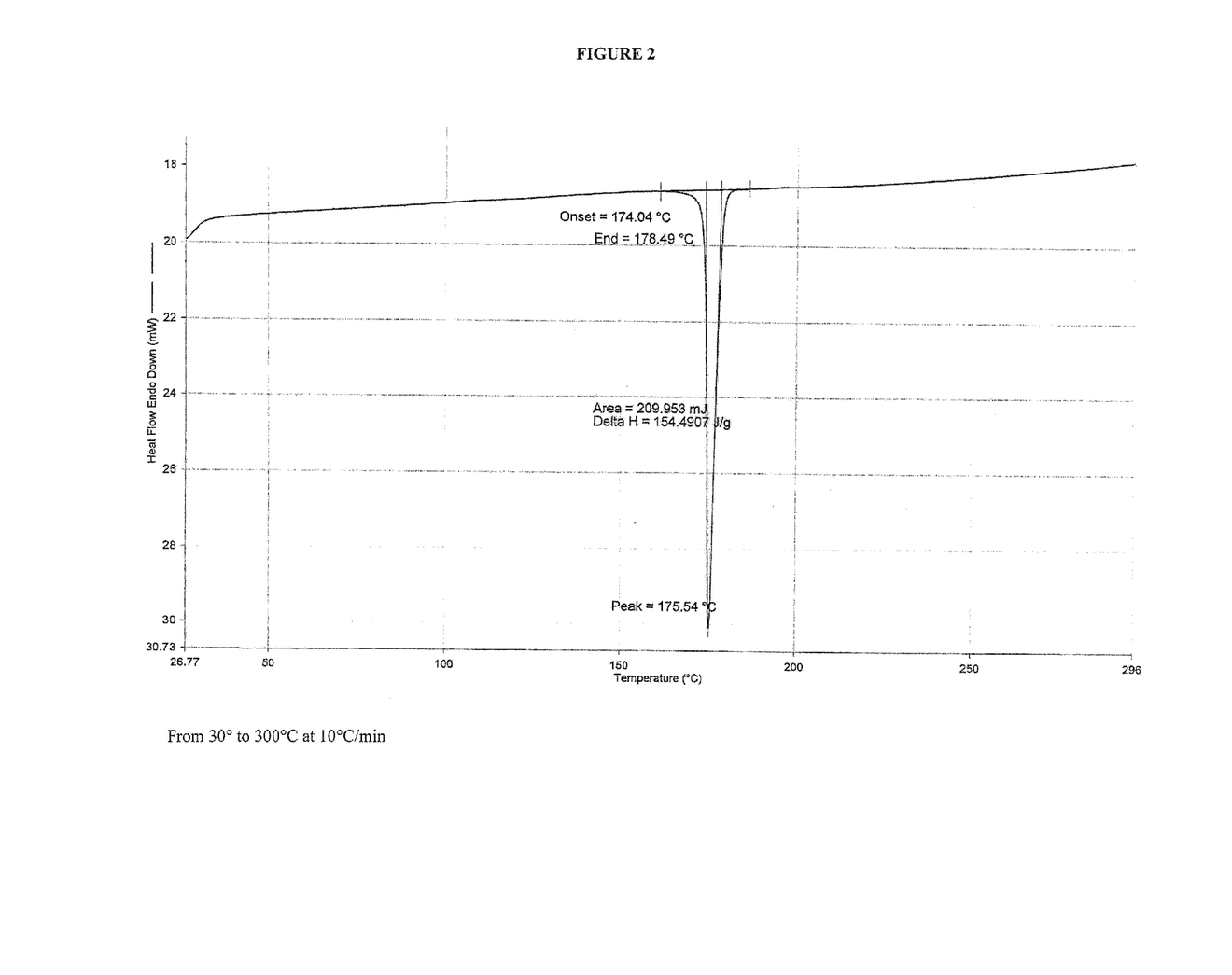
FIG. 2 is an example of a Differential Scanning calorimetry ("DSC") curve of crystalline 2-Chloro-N-(4-chloro-3-pyridin-2-ylphenyl)-4-methylsulfonylbenzamide designated as Form-SV.

In a further aspect of the present application, it relates to crystalline Form-SV of 2-Chloro-N-(4-chloro-3-pyridin-2-ylphenyl)-4-methylsulfonylbenzamide characterized by X-ray powder diffraction pattern substantially according to FIG. 1 and DSC isothermal pattern substantially according to FIG. 2.

In yet another aspect of the present application, it relates to process for preparing crystalline Form-SV of 2-Chloro-N-(4-chloro-3-pyridin-2-ylphenyl)-4-methylsulfonyl benzamide, characterized by X-ray powder diffraction pattern having at least five diffraction angle 2θ° peaks selected from peak set of 9.5, 10.7, 12.2, 15.8, 16.7, 17.4, 21.4, 24.0 and 26.0±0.2θ° and DSC isotherm comprising at least one endothermic peak ranging between 165 to 185° C., comprising the steps of:

(i) Providing a solution of 2-Chloro-N-(4-chloro-3-pyridin-2-ylphenyl)-4-methylsulfonyl benzamide in a $C_3$-$C_8$ ketone solvent or $C_1$-$C_2$ alcohol;

(ii) Heating the reaction to a temperature ranging between 45° C. to reflux temperature; (iii) Optionally filtering the reaction mass;

(iii) Cooling the reaction mass to a temperature of about 35° C. or below at a rate of not exceeding 1° C./min;

(iv) Filtering and isolating the solid material as pure crystalline 2-Chloro-N-(4-chloro-3-pyridin-2-ylphenyl)-4-methylsulfonylbenzamide designated as Form-SV.

Figure 3:
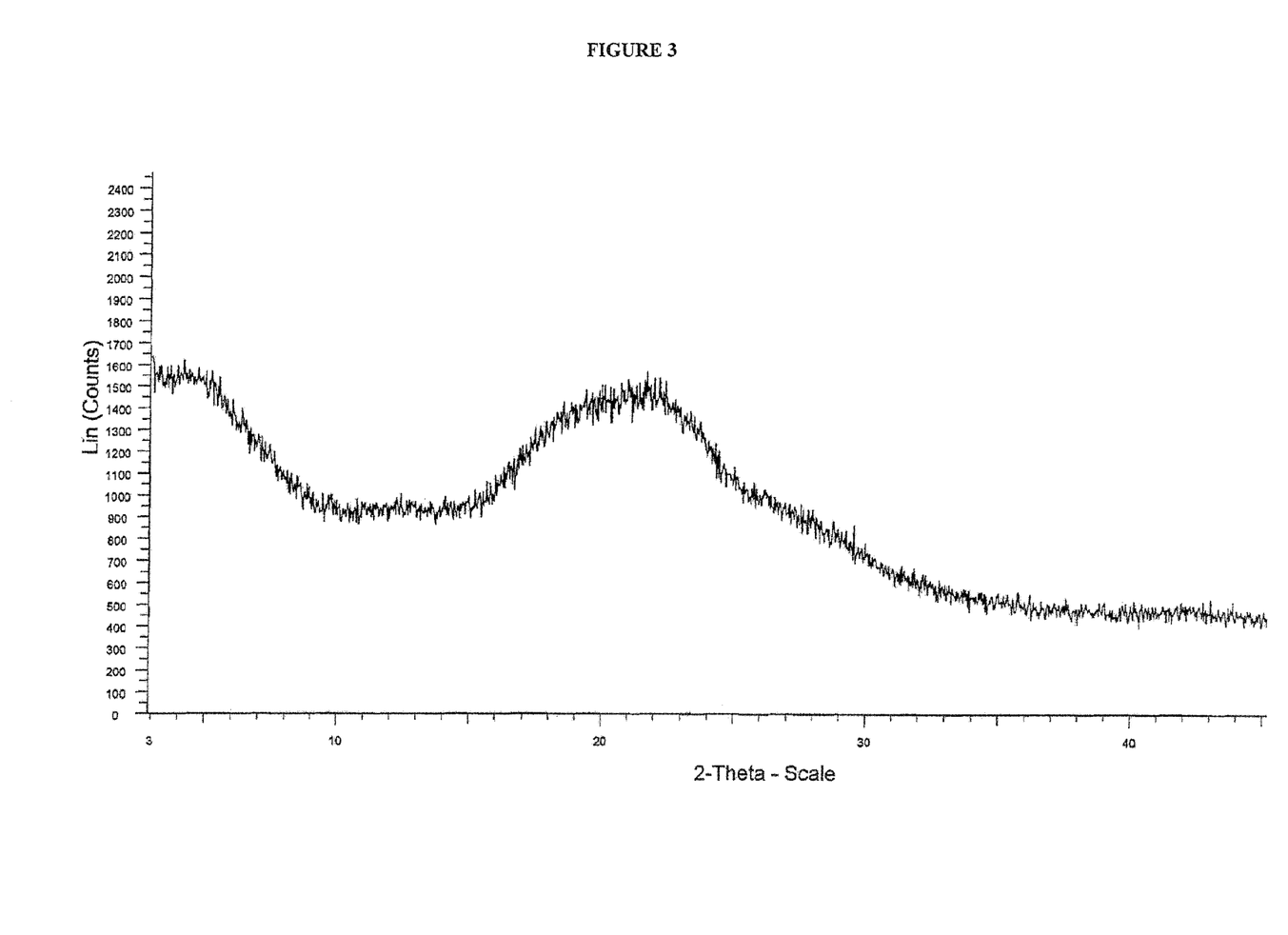
FIG. 3 is an example of X-ray powder diffraction ("XRPD") pattern of non-crystalline amorphous form of 2-Chloro-N-(4-chloro-3-pyridin-2-ylphenyl)-4-methylsulfonylbenzamide.

The present application also relates to a process for converting crystalline 2-chloro-N-(4-chloro 3-(pyridin-2-yl)phenyl)-4-(methylsulfonyl)benzamide into a non-crystalline form, comprising the steps of:

a) Providing a solution of 2-chloro-N-(4-chloro-3-(pyridin-2-yl)phenyl)-4-(methylsulfonyl)benzamide in an organic solvent selected from alcohols ($C_1$-$C_4$), halohydrocarbon solvent or organic ester solvent;

b) Heating the reaction mixture to a temperature ranging between 40° C. and the boiling point of the organic solvent used;

c) Filtering the reaction mixture and subjecting the filtrate to distillation to yield the residue;

d) Optionally repeating the steps a) to c);

e) Drying the material obtained from step c) or d) to obtain solid 2-chloro-N-(4-chloro-3-(pyridin-2-yl)phenyl)-4-(methylsulfonyl)benzamide in an amorphous form characterized by XRPD pattern as per FIG. 3.

In an aspect of the present application, this invention provides a non-crystalline amorphous form of (2-chloro-N-(4-chloro-3-(pyridin-2-yl)phenyl)-4-(methylsulfonyl)benzamide or Vismodegib (I).

In another aspect, solid forms of 2-Chloro-N-(4-chloro-3-pyridin-2-ylphenyl)-4-methylsulfonylbenzamide obtained by the process of the present invention are having HPLC purity greater than 99%.

In a further aspect, the present application also relates to a pharmaceutical compositions comprising crystalline Form SV or amorphous form of 2-Chloro-N-(4-chloro-3-pyridin-2-ylphenyl)-4-methylsulfonylbenzamide and at least one or more pharmaceutically acceptable excipients.

Further particular aspects of the invention are described in the detailed description part of the specification, wherever appropriate.

DETAILED DESCRIPTION

As set forth herein, embodiments of the present invention relate to a crystalline form of 2-Chloro-N-(4-chloro-3-pyridin-2-ylphenyl)-4-methylsulfonylbenzamide, designated as Form-SV and a process for preparation thereof. The invention of the present application further relates to pharmaceutical compositions comprising crystalline Form-SV or non-crystalline form of 2-chloro-N-(4-chloro-3-(pyridin-2-yl)phenyl)-4-(methylsulfonyl)benzamide useful in the treatment of cancer.

In an embodiment of the present application, the 2-Chloro-N-(4-chloro-3-pyridin-2-ylphenyl)-4-methylsulfonylbenzamide (I) crystalline Form-SV (I)

produced by the process of the present invention is characterized by—
i. X-ray powder diffraction pattern having at least five diffraction angle 2θ° peaks selected from peak set of 9.5, 10.7, 12.2, 15.8, 16.7, 17.4, 21.4, 24.0 and 26.0±0.2θ°
ii. DSC isotherm comprising at least one endothermic peak ranging between 165 to 185° C.

In a further embodiment of the present application, substantially pure 2-Chloro-N-(4-chloro-3-pyridin-2-ylphenyl)-4-methylsulfonylbenzamide crystalline Form-SV exhibits an X-ray powder diffraction pattern as shown in FIG. 1 and DSC isothermal pattern as shown in FIG. 2. The characteristic peaks and the d-pacing values of the new crystalline Foam-SV are tabulated in the

TABLE-1

Characteristic XRPD Peaks of Crystalline Form-SV

| S.No. | Angle (2θ°) ± 0.20 | d Spacing Value (A°) |
|---|---|---|
| 1. | 9.48 | 9.320 |
| 2. | 10.74 | 8.231 |
| 3. | 12.21 | 7.240 |
| 4. | 15.81 | 5.601 |
| 5. | 16.08 | 5.505 |
| 6. | 16.72 | 5.296 |
| 7. | 17.41 | 5.089 |
| 8. | 21.49 | 4.132 |
| 9. | 23.20 | 3.830 |
| 10. | 24.02 | 3.702 |
| 11. | 24.48 | 3.634 |
| 12. | 25.70 | 3.463 |
| 13. | 25.99 | 3.425 |
| 14. | 28.58 | 3.120 |

Minor variations in the observed 2 θ° angles values may be expected based on the analyst person, the specific XRPD diffractometer employed and the sample preparation technique. Further possible variations may also be expected for the relative peak intensities, which may be largely affected by the non-uniformity of the particle size of the sample. Hence, identification of the exact crystalline form of a compound should be based primarily on observed 2 theta angles with lesser importance attributed to relative peak intensities. The 2 theta diffraction angles and corresponding d-spacing values account for positions of various peaks in the X-ray powder diffraction pattern. D-spacing values are calculated with observed 2 theta angles and copper K α wavelength using the Bragg equation well known to those of having skill in the art of XRPD diffractometry science.

In view of possibility of marginal error in the assigning 2 theta angles and d-spacing, the preferred method of comparing X-ray powder diffraction patterns in order to identify a particular crystalline form is to overlay the X-ray powder diffraction pattern of the unknown form over the X-ray powder diffraction pattern of a known form. For example, one skilled in the art can overlay an X-ray powder diffraction pattern of an unidentified crystalline form of 2-Chloro-N-(4-chloro-3-pyridin-2-ylphenyl)-4-methylsulfonylbenzamide over FIG. 1 and readily determine whether the X-ray diffraction pattern of the unidentified form is substantially the same as the X-ray powder diffraction pattern of the crystalline Form-SV of this invention. If the X-ray powder diffraction pattern is substantially the same as FIG. 1, the previously unknown crystalline form of 2-Chloro-N-(4-chloro-3-pyridin-2-ylphenyl)-4-methylsulfonylbenzamide can be readily and accurately identified as the crystalline Form SV of this invention.

The new crystalline form of 2-Chloro-N-(4-chloro-3-pyridin-2-ylphenyl)-4-methyl sulfonylbenzamide, designated as Form-SV which is characterized by X-ray powder diffraction pattern as shown in FIG. 1 and DSC isothermal pattern as shown in FIG. 2 has been found to be quite stable and easy to handle and store for longer time without any measurable change in its morphology and physicochemical characteristics, while retaining its characteristics within the defined limits. This offers advantages for large scale manufacturing in terms of handling, storage, shelf life and favorable impurity profile.

In another embodiment of the present application, it provides process for preparing crystalline 2-Chloro-N-(4-chloro-3-pyridin-2-ylphenyl)-4-methylsulfonylbenzamide Form-SV, characterized by XRPD pattern having at least five diffraction angle 2θ° peaks selected from peak set of 9.5, 10.7, 12.2, 15.8, 16.7, 17.4, 21.4, 24.0 and 26.0±0.2θ° and DSC isotherm comprising at least one endothermic peak ranging between 165 to 185° C., comprising the steps of:
(i) Providing a solution of 2-Chloro-N-(4-chloro-3-pyridin-2-ylphenyl)-4-methylsulfonyl benzamide in a $C_3$-$C_8$ ketone solvent or $C_1$-$C_2$ alcohol;
(ii) Heating the reaction mixture to a temperature ranging between 45° C. to reflux temperature;
(iii) Optionally filtering the reaction mass;
(iv) Cooling the reaction mass to a temperature of about 35° C. or below at a rate of not exceeding 1° C./min;
(v) Filtering and isolating the solid material as pure crystalline 2-Chloro-N-(4-chloro-3-pyridin-2-ylphenyl)-4-methylsulfonylbenzamide designated as Form-SV.

The individual steps of the process according to the present invention for preparing 2-Chloro-N-(4-chloro-3-pyridin-2-ylphenyl)-4-methylsulfonylbenzamide crystalline Form-SV are detailed separately herein below.

Step i) comprises providing a solution of 2-Chloro-N-(4-chloro-3-pyridin-2-ylphenyl)-4-methylsulfonylbenzamide in a $C_3$-$C_8$ ketone solvent or $C_1$-$C_2$ alcohol;

2-Chloro-N-(4-chloro-3-pyridin-2-ylphenyl)-4-methylsulfonylbenzamide from any source or as synthesized by the process of the present invention is dissolved in an organic solvent selected from $C_3$-$C_8$ ketone solvent or $C_1$-$C_2$ alcohol. Amount of organic solvent (in mL) used to dissolve 2-Chloro-N-(4-chloro-3-pyridin-2-ylphenyl)-4-methylsulfonylbenzamide (in g) ranges from 10-35 times (v/w: mL/g).

$C_3$-$C_8$ ketone solvent used in the current step may be selected from acetone, acetophenone, butanone, methyl isobutyl ketone, methyl isopropyl ketone or ethyl isopropyl ketone. $C_1$-$C_2$ alcohol, when used as solvent in this reaction, may be selected from methanol or ethanol or a mixture thereof.

Step ii) comprises heating the reaction to a temperature ranging between 45° C. to reflux temperature;

Reaction mixture prepared in step i) is heated to a temperature ranging between 45° C. and the reflux temperature of the organic solvent used, to provide a clear solution. In one particular embodiment of the present application, wherein methanol was used as a solvent, the reaction mixture was heated to a temperature of ~60° C. After the clear solution is obtained, the reaction mass is maintained at the same raised temperature for a time duration of 40 mins to 4 hrs.

Step iii) which is optional, comprises filtering the reaction mass;

The reaction mass obtained in step ii) may optionally be filtered before proceeding further. Filtration may be performed at a raised temperature-suitable to avoid crystallization, and by methods well known in the art for e.g. by use of micron filter paper etc. The filtrate obtained from the filtration process may be re-heated to a temperature ranging between 45° C. to reflux temperature, in order to obtain the clear solution.

Step iv) comprises cooling the reaction mass to a temperature of about 35° C. or below at a rate of not exceeding 1° C./min Reaction mass obtained from step ii) or iii) is cooled down to 30-35° C. This temperature condition may be maintained for the time duration of 2-4 hrs. Further cooling of the reaction mass up to temperature of 0-5° C. may also be carried out as per requirement to perform crystallization. To obtain crystalline Form-SV of the present invention cooling of the solution shall be carried out gradually and slowly at a rate of not exceeding 1° C./min. In one particular embodiment of the present invention, the controlled cooling of the reaction mass from 55° C. to ~5° C. was performed in 2 hrs.

Step v) comprises filtering and isolating the solid material as pure crystalline 2-Chloro-N-(4-chloro-3-pyridin-2-ylphenyl)-4-methylsulfonylbenzamide designated as Form-SV.

The reaction mass obtained from step iv) is filtered to obtain a solid product. Filtration may be performed by using conventional methods for example but not limited to use of Buchner Funnel. Wet solid product obtained after filtration is subjected to drying at a temperature ranging between 40-60° C. or above. The drying process may be performed under reduced pressure condition, which may be suitably utilized by person skilled in the art in order to obtain the dried material. The drying process may be performed for time ranging from 2-4 hrs depending upon the physical attributes of the end product obtained i.e. Crystalline 2-chloro-N-(4-chloro-3-(pyridin-2-yl)phenyl)-4-(methylsulfonyl)benzamide (Form-SV).

Process of isolating crystalline form-SV may further comprise processes but not limited to conventional processes including scrapping and if required filtering from slurry which may be carried out at room temperature for the suitable durations to retain the crystalline form characteristics. Any 2-chloro-N-(4-chloro-3-(pyridin-2-yl)phenyl)-4-(methylsulfonyl)benzamide material i.e. it's any crystalline form or less stable form or impure/pure form obtained from any source or by any of the processes as mentioned here in this application or process already known in the prior art, may be utilized to result directly into the crystalline Form-SV of the present invention, by performing the process of the present application.

The process related impurities that appear in the impurity profile of the 2-chloro-N-(4-chloro-3-(pyridin-2-yl)phenyl)-4-(methylsulfonyl)benzamide may be substantially removed by the process of the present invention resulting in the formation pure crystalline Form-SV. The merit of the process according to the present invention resides in that—product obtained after drying is directly obtained as crystalline Form-SV. Said material is found to be adequately stable to handle and store for longer time (at least up to more than 6 months) without any significant or measurable change in its morphology and physicochemical characteristics. Melting range of the crystalline Form-SV of the present invention ranges from 175-180° C.

In another embodiment, the present application also relates to a process for converting crystalline 2-chloro-N-(4-chloro 3-(pyridin-2-yl)phenyl)-4-(methylsulfonyl)benzamide into a non-crystalline form, comprising the steps of:

a) Providing a solution of 2-chloro-N-(4-chloro-3-(pyridin-2-yl)phenyl)-4-(methylsulfonyl)benzamide in an organic solvent selected from alcohols ($C_1$-$C_4$), halohydrocarbon solvent or organic ester solvent;

b) Heating the reaction mixture to a temperature ranging between 40° C. and the boiling point of the organic solvent used;

c) Filtering the reaction mixture and subjecting the filtrate to distillation to yield the residue;

d) Optionally repeating the steps a) to c);

e) Drying the material obtained from step c) or d) to obtain solid 2-chloro-N-(4-chloro-3-(pyridin-2-yl)phenyl)-4-(methylsulfonyl)benzamide The individual steps of the process according to the present invention for converting crystalline 2-chloro-N-(4-chloro 3-(pyridin-2-yl)phenyl)-4-(methylsulfonyl)benzamide into a non-crystalline form are detailed separately herein below.

Step a) comprises providing a solution of 2-chloro-N-(4-chloro-3-(pyridin-2-yl)phenyl)-4-(methylsulfonyl)benzamide (I) in an organic solvent;

2-chloro-N-(4-chloro-3-(pyridin-2-yl)phenyl)-4-(methylsulfonyl)benzamide is dissolved in an organic solvent. Organic solvent may be selected from alcohols ($C_1$-$C_4$) selected from methanol, ethanol, IPA, n-propanol and the like, halohydrocarbon solvent selected from dichlormethane, dichloroethane and the like, or organic ester solvent selected from ethyl acetate and the like.

In one particular embodiment organic solvent used to prepare solution of 2-chloro-N-(4-chloro-3-(pyridin-2-yl)phenyl)-4-(methylsulfonyl)benzamide is methanol. The amount of solvent methanol (in mL) used in this step ranges from 30-50 times (v/w) w.r.t. weight (in g) of 2-chloro-N-(4-chloro-3-(pyridin-2-yl)phenyl)-4-(methylsulfonyl)benzamide taken for the reaction. In one particular embodiment, of the present application, for 1 gm of 2-chloro-N-(4-chloro-3-(pyridin-2-yl)phenyl)-4-(methylsulfonyl)benzamide, 50 mL methanol was used.

Any crystalline form of 2-chloro-N-(4-chloro-3-(pyridin-2-yl)phenyl)-4-(methylsulfonyl)benzamide may be used to proceed with this reaction. In a particular embodiment of this application, the crystalline Form-SV as described herein, was used as the starting material to be converted to the non-crystalline form.

Step b) comprises heating the reaction mixture to a temperature ranging between 40° C. and the boiling point of the organic solvent used;

Reaction mixture prepared in step a) is heated to a temperature ranging between 40° C. and the boiling point of the organic solvent used, to provide a clear solution. In one particular embodiment of the present application, wherein methanol was used as a solvent, temperature employed for the current step was 55-65° C. After the clear solution is obtained, the reaction mass is maintained at the same raised temperature for a time duration of 20 mins to 1 hr.

Step c) comprises filtering the reaction mixture and subjecting the filtrate to distillation to yield a residue The solution obtained from step b) is filtered at the same raised temperature wherein clear solution was achieved. Any conventional process for filtration may be employed to perform the current step. In one particular embodiment of the current application, filtration was performed by using micron filter paper. Filtration is performed to get impurities level/suspended particles controlled in the clear solution.

The filtrate obtained is subjected to distillation to remove the solvent. Distillation is carried out at temperature ranging between 40° C. and the boiling point of the organic solvent used. Distillation may optionally be performed under reduced pressure conditions. In one particular embodiment of the current application, distillation was performed under vacuum, wherein vacuum strength was slowly increased from 100 mm Hg to 650 mm Hg.

Step d) which is optional comprises repeating the steps a) to c)

The optional step d) which comprises repeating the steps a) to c) i.e. re-dissolving the residue obtained in step c) in organic solvent, heating the reaction mixture to a temperature ranging between 40° C. and the boiling point of the organic solvent used, filtering the reaction mixture and again subjecting the filtrate to distillation to yield a residue, is performed if required, to achieve the purity of greater than 99% (area %) by HPLC along with equilibration to impurity profile compliance. In view of maintaining the equilibrium to the impurity profile compliance, the process may require in-process quality checks to avoid unnecessary repetitions of the same process step.

Step e) comprises drying the material obtained from step c) or d) to obtain solid 2-chloro-N-(4-chloro-3-(pyridin-2-yl)phenyl)-4-(methylsulfonyl)benzamide.

The material obtained from step c) or d) is dried at a temperature ranging between 55-60° C. or above. The drying process may be performed under reduced pressure conditions. Reduced pressure conditions may be suitably utilized by person skilled in the art in order to obtain the dried material. The drying may be performed for time ranging from 20 mins to 4 hrs depending upon the physical attributes of the end product obtained.

In an embodiment of the present application, non-crystalline form of 2-chloro-N-(4-chloro 3-(pyridin-2-yl)phenyl)-4-(methylsulfonyl)benzamide, is obtained as an amorphous solid. The amorphous material obtained can be collected from the equipment using techniques such as by scraping, or by shaking the container, or using techniques specific to the particular apparatus optionally under nitrogen atmosphere.

As set forth above, an embodiment of the present invention relates to non-crystalline amorphous form of 2-Chloro-N-(4-chloro-3-pyridin-2-ylphenyl)-4-methylsulfonylbenzamide and a process for preparation thereof. Substantially pure amorphous form of 2-Chloro-N-(4-chloro-3-pyridin-2-ylphenyl)-4-methylsulfonylbenzamide (Vismodegib) exhibits an X-ray powder diffraction pattern substantially as shown in FIG. 3 indicating a solid form that lacks the long-range order (a characteristic of crystal) and having no pattern or structure.

Any crystalline 2-chloro-N-(4-chloro-3-(pyridin-2-yl)phenyl)-4-(methylsulfonyl)benzamide material obtained from any source or by any of the processes known in the prior art or as disclosed in this application, may be utilized to result directly into the amorphous 2-chloro-N-(4-chloro-3-(pyridin-2-yl)phenyl)-4-(methylsulfonyl)benzamide of the present invention.

The process related impurities that appear in the impurity profile of the 2-chloro-N-(4-chloro-3-(pyridin-2-yl)phenyl)-4-(methylsulfonyl)benzamide may be substantially removed by the process of the present invention resulting in the formation of pure amorphous form. The merit of the process according to the present invention resides in that—product obtained after drying is directly obtained as a non-crystalline amorphous form of 2-chloro-N-(4-chloro-3-(pyridin-2-yl)phenyl)-4-(methylsulfonyl)benzamide.

In an embodiment, the non-crystalline form of the present application may be in a pure amorphous form (100% amorphous), however, in certain embodiments, there is provided a substantially amorphous form, wherein the amorphous content in the solid Vismodegib is about 70% or 90% or 98% or more by weight.

X-ray diffraction provides a convenient and practical means for quantitative determination of the relative amounts of crystalline and/or amorphous forms in a solid mixture. X-ray diffraction is adaptable to quantitative applications because the intensities of the diffraction peaks, particularly long range peaks of a given compound in a mixture are proportional to the fraction of the corresponding powder in the mixture. The percent composition of amorphous Vismodegib in an unknown composition can be determined. Preferably, the measurements are made on solid powder of Vismodegib. The X-ray powder diffraction patterns of an unknown composition can be compared to known quantitative standards containing the pure amorphous form of Vismodegib to identify the percent ratio of amorphous/crystalline content. This is done by comparing the relative intensities of the peaks from the diffraction pattern of the unknown solid powder composition with a calibration curve derived from the X-ray diffraction patterns of pure known samples. The curve can be calibrated based on the X-ray powder diffraction pattern for the strongest peak or any distinctive peak from a pure sample of the crystalline form of Vismodegib. The calibration curve may be created in a manner known to those of skill in the art. For example, two or more artificial mixtures of crystalline forms of Vismodegib, at different amounts, may be prepared. In a non-limiting example, such mixtures may contain, 2%, 5%, 7%, 8%, and 10% of the amorphous form of Vismodegib. Then, X-ray diffraction patterns are obtained for each artificial mixture using standard X-ray diffraction techniques. Slight variations in peak positions, if any, may be accounted for by adjusting the location of the peak to be measured. The intensities of the selected characteristic peak(s) for each of the artificial mixtures are then plotted against the known weight percentages of the amorphous form. The resulting plot is a calibration curve that allows determination of the amount of the amorphous/crystalline form of Vismodegib in an unknown sample. For the unknown mixture of the crystalline and amorphous forms of Vismodegib, the intensities of the selected characteristic peak(s) in the mixture, relative to an intensity of this peak in a calibration mixture, may be used to determine the percentage of the given crystalline form in the composition, with the remainder determined to be the amorphous material.

The solid forms of 2-Chloro-N-(4-chloro-3-pyridin-2-ylphenyl)-4-methylsulfonyl benzamide obtained by the process of the present invention are having HPLC purity greater than 99%.

In another embodiment of the present invention the starting material 2-Chloro-N-(4-chloro-3-pyridin-2-ylphenyl)-4-methylsulfonylbenzamide (I) used to prepare the solid forms of the present invention is prepared by a process comprising the steps of:

i) Reacting 2-bromo-1-chloro-4-nitrobenzene with boronic ester to give compound of Formula (B);

(ii) Combining compound of Formula (B) with bromopyridine followed by reduction of the nitro compound (D) to obtain compound of Formula (E);

Boronated compound of Formula (B) is reacted with 2-bromo-pyridine to yield 2-(2-chloro-5-nitrophenyl)pyridine (D). Nitro compound (D) is then reduced by methods known in prior art to 4-chloro-3-(pyridin-2-yl)aniline (E).

(iii) Reacting the compound of Formula (E) with 2-chloro-4-(methylsulfonyl)benzoic acid of Formula (F) in the presence of a coupling reagent, organic base and an organic solvent to yield 2-Chloro-N-(4-chloro-3-pyridin-2-ylphenyl)-4-methylsulfonylbenzamide of Formula (I);

The coupling agent used in this reaction may be selected from Ethylchloroformate, 2-Chloro-4,6-dimethoxy-1,3,5-triazine (CDMT), 1,1'-carbonyldiimidazole (CDI) or N,N-dicyclohexyl carbodiimide (DCC). Organic base used in this reaction may be selected from triethylamine, N-methyl morpholine or 4-dimethylaminopyridine (DMAP) and organic solvent may be selected from a chlorinated hydrocarbon like DCM, cyclic ether like THF or an organic nitrile like acetonitrile.

(iv) Optionally purifying the 2-Chloro-N-(4-chloro-3-pyridin-2-ylphenyl)-4-methylsulfonylbenzamide obtained in step (iii);

In one of the embodiment, purification of 2-Chloro-N-(4-chloro-3-pyridin-2-ylphenyl)-4-methylsulfonylbenzamide obtained from step (iii) may be carried out by acid-base treatment for e.g. by using hydrochloric acid and sodium hydroxide. Purification may also be performed by treating with a suitable organic solvent for e.g. C1-C4 alcohols like methanol, ethanol, isopropanol or the mixture thereof.

The crystalline Form-SV or non-crystalline form of 2-chloro-N-(4-chloro-3-(pyridin-2-yl)phenyl)-4-(methylsulfonyl)benzamide described herein may be characterized by X-ray powder diffraction pattern (XRPD) and Thermal techniques such as differential scanning calorimetry (DSC) analysis. The samples were analyzed by XRPD on a Bruker AXS D8 Advance Diffractometer using X-ray source—Cu Kα radiation using the wavelength 1.5418 Å and lynx Eye detector. DSC was done on a Perkin Elmer Jade instrument. Illustrative examples of analytical data for the solid forms obtained in the examples are set forth in the FIGS. 1-3.

In a further aspect, the present application also relates to a pharmaceutical compositions comprising Form SV or amorphous form of 2-Chloro-N-(4-chloro-3-pyridin-2-ylphenyl)-4-methylsulfonylbenzamide and at least one or more pharmaceutically acceptable excipients.

In a further embodiment according to the specification, the invention also relates to a composition containing crystalline Form-SV or amorphous form of 2-chloro-N-(4-chloro-3-(pyridin-2-yl)phenyl)-4-(methylsulfonyl)benzamide, in which at least 95%, by total weight of 2-chloro-N-(4-chloro-3-(pyridin-2-yl)phenyl)-4-(methylsulfonyl)benzamide in the composition, is the crystalline Form-SV or the amorphous form of 2-chloro-N-(4-chloro-3-(pyridin-2-yl)phenyl)-4-(methylsulfonyl)benzamide. In yet another embodiment of the invention, the composition may be substantially free of any other forms of 2-chloro-N-(4-chloro-3-(pyridin-2-yl)phenyl)-4-(methylsulfonyl)benzamide.

The crystalline Form-SV or amorphous form of 2-chloro-N-(4-chloro-3-(pyridin-2-yl)phenyl)-4-(methylsulfonyl) benzamide obtained by the process of the present application may be formulated as solid compositions for oral administration in the form of capsules, tablets, pills, powders or granules. In these compositions, the active product is mixed with one or more pharmaceutically acceptable excipients. The drug substance can be formulated as liquid compositions for oral administration including solutions, suspensions, syrups, elixirs and emulsions, containing solvents or vehicles such as water, sorbitol, glycerin, propylene glycol or liquid paraffin.

In one embodiment of the present invention, it also includes premix comprising one or more pharmaceutically acceptable excipients in the range of 1 to 50% w/w with crystalline Form-SV or amorphous form of 2-chloro-N-(4-chloro-3-(pyridin-2-yl)phenyl)-4-(methyl sulfonyl)benzamide, while retaining the polymorphic nature of the premix.

The compositions for parenteral administration can be suspensions, emulsions or aqueous or non-aqueous sterile solutions. As a solvent or vehicle, propylene glycol, polyethylene glycol, vegetable oils, especially olive oil, and injectable organic esters, e.g. ethyl oleate, may be employed. These compositions can contain adjuvants, especially wetting, emulsifying and dispersing agents. The sterilization may be carried out in several ways, e.g. using a bacteriological filter, by incorporating sterilizing agents in the composition, by irradiation or by heating. They may be prepared in the form of sterile compositions, which can be dissolved at the time of use in sterile water or any other sterile injectable medium.

Pharmaceutically acceptable excipients used in the compositions comprising crystalline Form-SV or amorphous form of 2-chloro-N-(4-chloro-3-(pyridin-2-yl)phenyl)-4-(methylsulfonyl)benzamide of the present application include, but are but not limited to diluents such as starch, pregelatinized starch, lactose, powdered cellulose, microcrystalline cellulose, dicalcium phosphate, tricalcium phosphate, mannitol, sorbitol, sugar and the like; binders such as acacia, guar gum, tragacanth, gelatin, pre-gelatinized starch and the like; disintegrants such as starch, sodium starch glycolate, pregelatinized starch, Croscarmellose sodium, colloidal silicon dioxide and the like; lubricants such as stearic acid, magnesium stearate, zinc stearate and the like; glidants such as colloidal silicon dioxide and the like; solubility or wetting enhancers such as anionic or cationic or neutral surfactants, waxes and the like. Other pharmaceutically acceptable excipients that are of use include but not limited to film formers, plasticizers, colorants, flavoring agents, sweeteners, viscosity enhancers, preservatives, antioxidants and the like.

EXAMPLE

Example a)

Preparation of 2-chloro-N-(4-chloro-3-(pyridin-2-yl)phenyl)-4-(methyl sulfonyl)benzamide (I)

3.2 g 2-Chloro-4,6-dimethoxy-1,3,5-traizine (CDMT) was charged to a mixture of 2.8 g 2-chloro-4-(methylsulfonyl) benzoic acid (Formula F) in 80 mL methylene dichloride (MDC) under nitrogen atmosphere at 25-30° C. and stirred for about 20 mins 4.9 g N-methyl morpholine (NMM) was added to the reaction mixture over period of about 15 mins maintaining temperature of 20-30° C. Reaction mixture was maintained under stirring at this temperature for about 3 hrs. 2 g 4-chloro-3-(pyridin-2-yl)benzenamine (Formula E) was then added to the reaction mixture and stirring was done for additional 3 hrs at same temperature. Then the temperature of reaction mixture was raised to 35-40° C. and stirring was done, intermittently checking reaction progress by TLC. On completion of the reaction, reaction mixture was cooled to 20-30° C. and quenched with 40 mL water. Organic layer was separated and the aqueous layer was washed with 20 mL MDC. MDC organic layer was collected and washed twice with 40 mL saturated sodium bicarbonate solution followed by a water washing (40 mL). Organic layer was dried over sodium sulphate and solvent was distilled off under vacuum at 35-45° C. to obtain a residue. To this residue, 30 mL Iso-propyl alcohol (IPA) was added and reaction temperature was raised to 60-70° C., wherein stirring was performed for about 30 mins followed by slow cooling to 20-30° C. Reaction was maintained for about 1 hr at same temperature under stirring. The precipitated product was filtered on Buchner funnel, washed with 10 mL IPA and dried at 40-45° C. under vacuum to get 2.5 g 2-chloro-N-(4-chloro-3-(pyridin-2-yl)phenyl)-4-(methylsulfonyl)benzamide (I) having HPLC area purity of 99.3%.

Example-01

Process for Preparation of Crystalline 2-chloro-N-(4-chloro-3-(pyridin-2-yl)phenyl)-4-(methylsulfonyl)benzamide (Form-SV)

0.5 gm 2-chloro-N-(4-chloro-3-(pyridin-2-yl)phenyl)-4-(methylsulfonyl)benzamide (I) was charged to a 100 ml RBF. Further 7 ml acetone was added to the RBF and temperature was raised to ~55° C. to get clear solution. Same temperature was maintained for ~50 mins. The solution was then filtered through micron filter paper at same temperature. Filtrate was then charged to 100 ml RBF and solution was heated to a temperature of about 50° C. to get clear solution. Solution was maintained at same temperature for ~45 mins. Solution was gradually cooled to ~30° C. Gradually temperature was further lowered to 0-5° C., and solution was maintained at this temperature for ~2.5 hrs. The precipitated solid was filtered on Buchner funnel to get the wet product. The wet product was dried under vacuum at ~45° C. for 3 hrs and unloaded to afford 0.30 gm crystalline 2-chloro-N-(4-chloro-3-(pyridin-2-yl)phenyl)-4-(methylsulfonyl)benzamide Form-SV having the XRPD diffractogram and DSC isotherm as shown in FIGS. 1 and 2 resp.

Yield: 0.30 gm, HPLC purity: 99.64%

Example-02

Process for Preparation of Crystalline 2-chloro-N-(4-chloro-3-(pyridin-2-yl)phenyl)-4-(methylsulfonyl)benzamide (Form-SV)

1.0 gm 2-chloro-N-(4-chloro-3-(pyridin-2-yl)phenyl)-4-(methylsulfonyl)benzamide (I) was charged to a 100 ml RBF. Further 30 ml methanol was added to the RBF and temperature was raised to ~60° C. Same temperature was maintained for 3 hours. Solution was gradually cooled to ~25° C. Solution was maintained at this temperature for ~2 hrs. The precipitated solid was filtered on Buchner funnel to get the wet product. The wet product was dried under vacuum at ~45° C. for 3 hrs and unloaded to afford 0.7 gm crystalline 2-chloro-N-(4-chloro-3-(pyridin-2-yl)phenyl)-4-(methylsulfonyl) benzamide Form-SV having the XRPD diffractogram and DSC isotherm similar to the figures shown in FIGS. 1 and 2 resp.

Yield: 0.7 gm, HPLC purity: 99.66%

Example-03

Process for Converting Crystalline 2-chloro-N-(4-chloro-3-(pyridin-2-yl)phenyl)-4-(methylsulfonyl) benzamide into a Non-Crystalline Form 1 gm 2-chloro-N-(4-chloro-3-(pyridin-2-yl)phenyl)-4-(methylsulfonyl)benzamide (I) was charged to 100 ml RBF. 50 ml methanol was added to the reaction mass and heating was performed to about 60° C. to get clear solution. Temperature of 55-65° C. was maintained for 30 mins after getting clear solution. At the same raised temperature, the solution was filtered through micron filter paper. The filtrate was then charged to the rotavapor flask and distillation was performed at about 55° C. under vacuum. Vacuum was applied slowly from 100 mm/Hg and increased to 650 mm/Hg. After complete distillation of solvent, material was dried under vacuum at 60° C. for 25 min with high RPM. Further 50 ml methanol was charged to the residue obtained in rotavapour flask. The solution was heated to 60° C. to get clear solution without applying vacuum. After getting clear solution, temperature of 60° C. was maintained for 30 mins. Then distillation was performed again at 50-60° C. under vacuum. As earlier, vacuum was applied slowly from 100 mm/Hg and increased to 650 mm/Hg. The material obtained after distillation was dried under vacuum at 55° C. for 2.5 hrs to afford non-crystalline amorphous form of 2-chloro-N-(4-chloro-3-(pyridin-2-yl)phenyl)-4-(methylsulfonyl)benzamide having the XRPD diffractogram as shown in FIG. 3.

Yield: 0.96 gm, HPLC purity: 99.43%

Example-04

Process for Converting Crystalline 2-chloro-N-(4-chloro-3-(pyridin-2-yl)phenyl)-4-(methylsulfonyl) benzamide into a Non-Crystalline Form

1 g 2-chloro-N-(4-chloro-3-(pyridin-2-yl)phenyl)-4-(methylsulfonyl)benzamide (I) was charged to 100 ml RBF having 50 ml methanol. The temperature was raised to about 65° C. till a clear solution is attained. Temperature of 60-65° C. was maintained for 40 mins after getting clear solution. At the same raised temperature, the solution was filtered through micron filter paper. The filtrate was then charged to the rotavapour flask and distillation was performed at about 50° C. under vacuum. Vacuum was applied slowly from 100 mm/Hg and increased to 650 mm/Hg. After complete distillation of solvent, material obtained was dried under vacuum at 60° C. for 30 min with high RPM. Further 55 ml methanol was charged to the residue obtained in rotavapour flask. Without applying vacuum the solution was heated again to about 65° C. to get clear solution. After getting clear solution, temperature of about 60° C. was maintained for 25 mins. Then distillation was performed again at 50-60° C. under vacuum. Vacuum was applied slowly from 100 mm/Hg and increased to 650 mm/Hg. The material obtained after distillation was dried under vacuum at 60° C. for 3 hrs to afford non-crystalline amorphous form of 2-chloro-N-(4-chloro-3-(pyridin-2-yl)phenyl)-4-(methylsulfonyl)benzamide having the XRPD diffractogram similar to the one shown in FIG. 3.

Yield: 0.92 gm, HPLC purity: ~99%

While the foregoing pages provide a detailed description of the preferred embodiments of the invention, it is to be understood that the description and examples are illustrative only of the principles of the invention and not limiting. Furthermore, as many changes can be made to the invention without departing from the scope of the invention, it is intended that all material contained herein be interpreted as illustrative of the invention and not in a limiting sense.

We claim:

1. Crystalline 2-Chloro-N-(4-chloro-3-pyridin-2-ylphenyl)-4-methylsulfonylbenzamide (I) designated as Form-SV, (I)

characterized by XRPD pattern having at least five diffraction angle 2θ° peaks selected from peak set of 9.5, 10.7, 12.2, 15.8, 16.7, 17.4, 21.4, 24.0 and 26.0±0.2θ°.

2. Crystalline 2-Chloro-N-(4-chloro-3-pyridin-2-ylphenyl)-4-methylsulfonylbenzamide Form-SV, according to claim 1, further characterized by DSC isotherm comprising at least one endothermic peak ranging between 165 to 185° C.

3. A process for preparing crystalline 2-Chloro-N-(4-chloro-3-pyridin-2-ylphenyl)-4-methylsulfonylbenzamide Form-SV, characterized by XRPD pattern having at least five diffraction angle 2θ° peaks selected from peak set of 9.5, 10.7, 12.2, 15.8, 16.7, 17.4, 21.4, 24.0 and 26.0±0.2θ° and DSC isotherm comprising at least one endothermic peak ranging between 165 to 185° C., comprising the steps of:

(i) providing a solution of 2-Chloro-N-(4-chloro-3-pyridin-2-ylphenyl)-4-methyl sulfonyl benzamide in a $C_3$-$C_8$ ketone solvent or $C_1$-$C_2$ alcohol;

(ii) heating the reaction mixture to a temperature ranging between 45° C. to reflux temperature;

(iii) optionally filtering the reaction mass;

(iv) cooling the reaction mass to a temperature of about 35° C. or below at a rate of not exceeding 1° C./min; and

(v) filtering and isolating the solid material as pure crystalline 2-Chloro-N-(4-chloro-3-pyridin-2-ylphenyl)-4-methylsulfonylbenzamide designated as Form-SV.

4. A process for preparing crystalline 2-Chloro-N-(4-chloro-3-pyridin-2-ylphenyl)-4-methylsulfonylbenzamide Form-SV, according to claim 3, wherein $C_3$-$C_8$ ketone solvent is selected from acetone, acetophenone, butanone, methyl isobutyl ketone, methyl isopropyl ketone or ethyl isopropyl ketone and $C_1$-$C_2$ alcohol is selected from methanol, ethanol or a mixture thereof.

5. A process for preparing crystalline 2-Chloro-N-(4-chloro-3-pyridin-2-ylphenyl)-4-methylsulfonylbenzamide Form-SV, characterized by XRPD pattern having at least five diffraction angle 2θ° peaks selected from peak set of 9.5, 10.7, 12.2, 15.8, 16.7, 17.4, 21.4, 24.0 and 26.0±0.2θ° and DSC isotherm comprising at least one endothermic peak ranging between 165 to 185° C., comprising the steps of:

i) reacting 2-bromo-1-chloro-4-nitrobenzene with boronic ester to give compound of Formula (B);

17 ii) combining compound of Formula (B) with bromo-pyridine followed by reduction of the nitro compound (D) to obtain compound of Formula (E);

iii) reacting the compound of Formula (E) with 2-chloro-4-(methyl sulfonyl)benzoic acid of Formula (F) in the presence of a coupling reagent, organic base and an organic solvent selected from chlorinated hydrocarbon, cyclic ether or an organic nitrile, to yield 2-Chloro-N-(4-chloro-3-pyridin-2-ylphenyl)-4-methylsulfonylbenzamide of Formula (I);

+

18

-continued iv) optionally, purifying the 2-Chloro-N-(4-chloro-3-pyridin-2-ylphenyl)-4-methyl sulfonyl benzamide obtained in step (iii);

v) providing a solution of 2-Chloro-N-(4-chloro-3-pyridin-2-ylphenyl)-4-methyl sulfonyl benzamide in a $C_3$-$C_8$ ketone solvent or $C_1$-$C_2$ alcohol;

vi) heating the reaction mixture to a temperature ranging between 45° C. to reflux temperature;

vii) optionally filtering the reaction mass;

viii) cooling the reaction mass to a temperature of about 35° C. or below at a rate of not exceeding 1° C./min; and ix) filtering and isolating the solid material as pure crystalline 2-Chloro-N-(4-chloro-3-pyridin-2-ylphenyl)-4-methyl sulfonylbenzamide designated as Form-SV.

6. A process for preparing crystalline 2-Chloro-N-(4-chloro-3-pyridin-2-ylphenyl)-4-methylsulfonylbenzamide Form-SV, according to claim 5, wherein in step (iii):

a) the coupling reagent used is selected from Ethylchloroformate, 2-Chloro-4,6-dimethoxy-1,3,5-traizine (CDMT), 1,1'-carbonyldiimidazole (CDI) or N,N-dicyclohexylcarbodiimide (DCC);

b) organic base is selected from triethylamine, N-methyl morpholine (NMM) or 4-dimethylaminopyridine (DMAP);

c) organic solvent is selected from a chlorinated hydrocarbon, cyclic ether or an organic nitrile.

7. A process for preparing crystalline 2-Chloro-N-(4-chloro-3-pyridin-2-ylphenyl)-4-methylsulfonylbenzamide Form-SV, according to claim 5, wherein $C_3$-$C_8$ ketone solvent is selected from acetone, acetophenone, butanone, methyl isobutyl ketone, methyl isopropyl ketone or ethyl isopropyl ketone and $C_1$-$C_2$ alcohol is selected from methanol, ethanol or a mixture thereof.

8. A pharmaceutical composition according to claim 1, comprising crystalline Form SV of 2-Chloro-N-(4-chloro-3-pyridin-2-ylphenyl)-4-methylsulfonylbenzamide and at least one or more pharmaceutically acceptable excipients.

* * * * *